United States Patent [19]

Lowery et al.

[11] Patent Number: 5,374,247

[45] Date of Patent: Dec. 20, 1994

[54] METHOD OF DELIVERING A SUBSTANCE TO A FALLOPIAN TUBE

[75] Inventors: Guy R. Lowery, Mission Viejo; Steven R. Bacich, Laguna Niguel; Keith Tholin, Irvine; Gary M. Woker, Escondido, all of Calif.

[73] Assignee: Imagyn Medical, Inc., Laguna Niguel, Calif.

[21] Appl. No.: 53,150

[22] Filed: Apr. 26, 1993

Related U.S. Application Data

[63] Continuation-in-part of Ser. No. 780,871, Oct. 18, 1991, abandoned.

[51] Int. Cl.$^5$ .................... A61M 31/00; A61M 5/00
[52] U.S. Cl. ........................................ 604/55; 604/271
[58] Field of Search ......................... 604/49–55, 604/271, 264; 600/33–35

[56] References Cited

U.S. PATENT DOCUMENTS

| | | |
|---|---|---|
| 4,243,040 | 1/1981 | Beecher . |
| 4,271,839 | 6/1981 | Fogarty et al. . |
| 4,321,915 | 3/1982 | Leighton et al. ................ 128/4 |
| 4,437,857 | 3/1984 | Goldstein et al. . |
| 4,530,698 | 7/1985 | Goldstein et al. . |
| 4,604,094 | 8/1986 | Shook . |
| 5,108,366 | 4/1992 | Schatz . |
| 5,163,927 | 11/1992 | Woker et al. . |
| 5,171,305 | 12/1992 | Schickling et al. . |
| 5,236,423 | 8/1993 | Mix et al. ........................ 604/271 |
| 5,259,364 | 11/1993 | Bob et al. ........................ 128/4 |

OTHER PUBLICATIONS

"Transcervical Intra Fallopian Endoscopy-Fallposcopy", *Focus on Reproduction*, Jan. 1993, Bauer et al.

"Nonoperative Embryo Transfer to the Fallopian Tube", Jansen et al., *The New England Journal of Medicine*, pp. 288–290, Aug. 4, 1988.

"Retrograde tubal transfer of human embryos", Risquez et al. i Human Reproduction, pp. 185–188, 1990.

"Gemete intrafallopian transfer by hysteroscopy as an alternative treatment for infertility", Possati et al. *Fertility and Sterility*, vol. 56, No. 3, Sep. 1991, pp. 496–499.

"Transcervical access and intra-luminal imaging of the Fallopian tube in the non-anaesthetized patient; Preliminary results using a new technique for Fallopian access", Otmar Bauer et al., Human Reproduction, vol. 7 suppl. 1, pp. 7–11, 1992.

"The linear everting catheter: a nonhysteroscopic, transvaginal technique for access and a microendoscopy of the fallopian tube", Pearlstone et al., *Fertility and Sterility*, vol. 68 No. 4, Oct. 1992.

Primary Examiner—John D. Yasko
Assistant Examiner—Adam J. Cermak
Attorney, Agent, or Firm—Gordon L. Peterson

[57] ABSTRACT

A method of delivering a substance to a fallopian tube of a patient which includes obtaining transcervical access to a fallopian tube with an everting catheter. Access to the fallopian tube is obtained by everting an everting element of the everting catheter in the fallopian tube. A substance selected from the group consisting of biological material and cytotoxic agents is then delivered through the everting catheter to the fallopian tube to deposit the substance in the fallopian tube.

24 Claims, 6 Drawing Sheets

Fig. 4

METHOD OF DELIVERING A SUBSTANCE TO A FALLOPIAN TUBE

This application is a continuation-in-part of application Ser. No. 780,871 filed on Oct. 18, 1991 and entitled Apparatus and Method for Independent Movement of an Instrument within a Linear Eversion Catheter (now abandoned).

BACKGROUND OF THE INVENTION

This invention provides a method for dealing with problems of infertility and of a tubal or ectopic pregnancy. In one treatment for infertility, biological material such as gametes and zygotes are deposited into the fallopian tube. Unfortunately, it is difficult to gain access to the fallopian tubes in order to make this deposition.

Generally, there are two approaches for gaining access to a fallopian tube. One is the laparoscopic approach to a distal region of the fallopian tube. The second and preferred approach which is less invasive is placing of a catheter transcervically into the fallopian tube. This requires passing of the catheter through the cervix, uterus and ostium of the fallopian tube and then navigating the fallopian tube an appropriate distance. One problem with this approach is getting the catheter to pass from the uterus through the ostium into the fallopian tube.

Various techniques have been employed in an effort to gain access to the fallopian tube from the uterus. One approach is to use tactile feel, but this requires a high amount of dexterity for the clinician and there is no assurance that the catheter has been placed within the fallopian tube. For ectopic therapy, tactile feel will not locate the ectopic in the fallopian tube. The catheter can be guided ultrasonically, but this involves additional discomfort to the patient and also does not provide a high level of assurance that the fallopian tube has been accessed.

Hysteroscopic guidance may also be used but this requires insufflation of the uterus which can have a negative effect on the placement of biological material and involves additional discomfort to the patient when employed on an outpatient basis. It is also known to utilize an everting catheter to gain access to the fallopian tubes and to guide an instrument such as an endoscope into the fallopian tube, but so far as we are aware, everting catheters have not been used to deposit biological material or to eliminate ectopic pregnancies.

The catheters used previously for the deposition of biological material were single lumen catheters constructed of polytetrafluoroethylene. These catheters were inserted into the fallopian tube using tactile feel, hysteroscopic guidance or ultrasonic guidance and a syringe at the proximal end of the catheter was used to expel the biological material into the fallopian tube. In addition to these three techniques, it is also known to use guidewires for placing the single lumen catheter within the fallopian tube and access to the ostium of the fallopian tube was obtained using a stiffer guiding catheter which directs the single lumen catheter to the ostium.

SUMMARY OF THE INVENTION

This invention provides a method for depositing biological material and cytotoxic agents in the fallopian tubes which generally overcomes the disadvantages noted above. With this invention, the fallopian tubes are accessed with greater certainty and with less patient discomfort and the desired region for the depositing of the biological material or cytotoxic agent can be located.

With this invention, transcervical access to a fallopian tube is obtained with an everting catheter. This avoids the more invasive laparoscopic approach and the everting catheter can obtain access to the fallopian tube with greater certainty and less patient discomfort than other transcervical access techniques. The step of obtaining access includes everting an everting element of the everting catheter in the fallopian tube. Next, the substance is delivered through the everting catheter into the fallopian tube to deposit the substance in the fallopian tube.

For example, if the substance to be deposited is a biological material it may be gametes or embryos. If an ectopic pregnancy is to be treated, the substance to be deposited may be a cytotoxic agent of any appropriate nature, such as prostaglandins or methatrexate, to deal with the ectopic. Typically, although not necessarily, the substance is in liquid form.

Various specific features of the invention may be used in carrying out of the method of this invention. For example, the substance may be provided within the everting catheter prior to the step of obtaining and with the everting element inverted and the step of delivering may include everting the everting element in the fallopian tube sufficiently to deposit the substance in the fallopian tube. Alternatively, an elongated flexible delivery catheter can be inserted through a substantial length of the everting catheter and the step of delivering can be carried out through the delivery catheter. In this latter case, the substance may be loaded into a distal end of the delivery catheter with the delivery catheter extending beyond a distal end of the everting catheter and with the tube outside the body of the patient. The delivery catheter may be inserted through the everting catheter after the everting catheter has been inserted through the cervix into the uterus and either before or after eversion of the everting element into the fallopian tube. Alternatively, the substance may be loaded into at least one of the delivery catheter and a delivery device and then delivered through the delivery catheter.

In order to view the fallopian tube, an elongated flexible endoscope may be extended sufficiently through the everting catheter so it can be used to view the fallopian tube distally of the everting catheter. The fallopian tube is then viewed with the endoscope to locate a desired region of the fallopian tube and the substance is then deposited at such desired region. The endoscope may be withdrawn prior to depositing of the substance in the fallopian tube and in this event, the substance may be delivered through a delivery catheter which extends through a substantial length of the everting catheter or directly through the everting catheter without using a delivery catheter.

According to one aspect of this invention, the delivery catheter includes an elongated flexible endoscope which extends sufficiently through the everting catheter so it can be used for viewing of the fallopian tube distally of the everting catheter. In this event, the substance can be delivered through the delivery catheter with the endoscope in place in the fallopian tube. For example, the endoscope may have a working lumen and the substance can be delivered through the working lumen to the desired region of the fallopian tube. Alternatively, the delivery catheter may include an elongated flexible tube removably coupled to the endoscope, and in this event, the substance is delivered through the tube. One advantage of this latter feature is that the tube may be disposable and the endoscope can be re-sterilized for use in another patient.

The everting catheter may include an outer catheter having an outer catheter lumen, an inner catheter movable in the outer catheter lumen and having an inner catheter lumen and an everting element coupled to the outer and inner catheter. With this construction, if an endoscope is employed, it may be provided within the inner catheter lumen and the everting element and this may be accomplished during the obtaining of access to the fallopian tube or after the everting catheter has been everted into the fallopian tube. Typically, the everting element is everted to gain access from the uterus to the fallopian tube. If the endoscope is withdrawn prior to depositing of the substance, then the substance can be delivered through the inner catheter lumen and the everting element to the fallopian tube.

When the method of this invention employs an endoscope in the inner catheter lumen, the everting element when inflated grips the endoscope and can be used to advance and retract the endoscope. In order to axially position the endoscope, it may be necessary to remove this gripping force from the endoscope so that the endoscope can be freely moved relative to the everting element. Although this could be accomplished by deflating the everting element, preferably it is carried out by introducing a flush solution between the everting element and the endoscope where the everting element grips the endoscope. This removes the gripping force sufficiently so that the endoscope can be moved relative to the everting element while the flush solution is between the everting element and the endoscope. This flush solution also has the advantage of clearing debris from the field of view, helps keep the lens of the endoscope clear and distends tissue at the distal end of the everting element to further assist viewing. This technique is described more specifically in common assignee's copending parent application Ser. No. 780,871 filed on Oct. 18, 1991.

Another feature of this invention is the catheter which includes a flexible tube removably coupled to an endoscope. A releasable coupling releasably couples the tube to the endoscope body with the tube extending longitudinally along the endoscope body. The endoscope body and the flexible tube have distal ends and preferably the distal ends are adjacent. Although the releasable coupling may be on the flexible tube or be separate from both the endoscope and the flexible tube, in a preferred construction, the releasable coupling includes spaced arms on the endoscope body for releasably gripping the tube. When this construction is to be used for biological material deposition, the tube is preferably constructed of a material which inert to the biological material and one example of a suitable tube material is polytetrafluoroethylene.

The invention, together with additional features and advantages thereof may best be understood by reference to the following description taken in connection with the accompanying illustrative drawings.

DESCRIPTION OF THE PREFERRED EMBODIMENT

Figure 1:
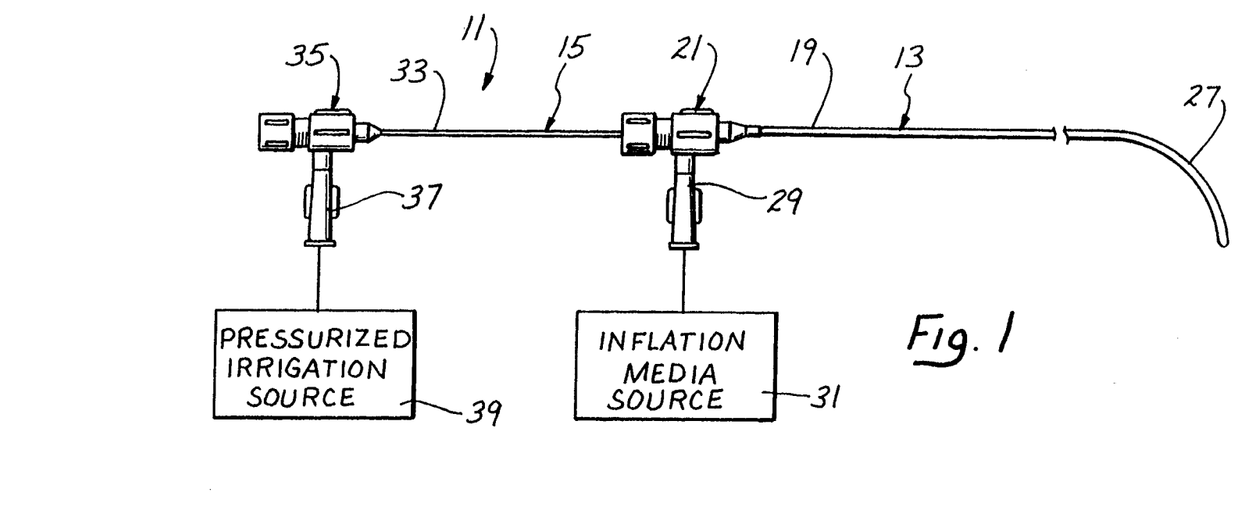
FIG. 1 is an elevational view of an everting catheter which can be used in carrying out the method of this invention. The everting element is inverted.
Figure 2:
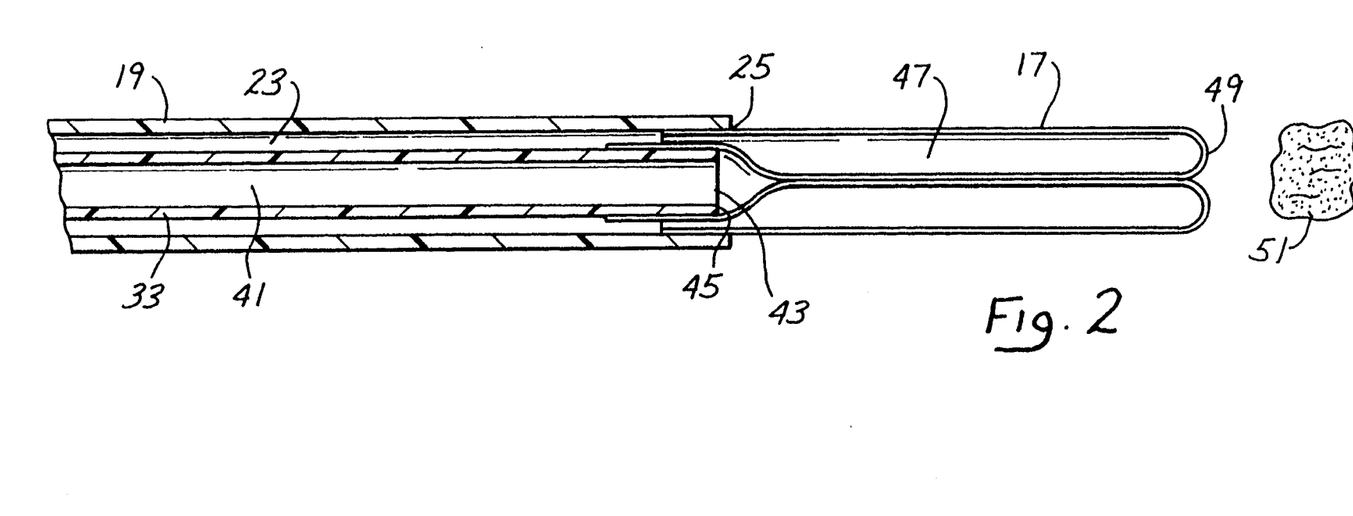
FIG. 2 is an enlarged, fragmentary, axial sectional view of a distal region of the everting catheter of FIG. 1 with the everting element being partially everted and in a position to have a substance loaded into the everting element.

FIG. 1 shows an everting catheter 11 which generally comprises an outer catheter 13, an inner catheter 15 and an everting element 17 (FIG. 2). The outer catheter 13 includes an elongated, flexible catheter body 19 and an outer catheter fitting 21 coupled to the proximal end of the catheter body 19. The outer catheter 13 has an outer catheter lumen 23 (FIG. 2) which extends for the full length of the catheter body 19 and opens at a distal opening 25 (FIG. 2). The distal opening 25 need not be at the distal end of the catheter body 19.

The catheter body 19 has a distal end portion 27 which, in its unstressed condition, may be straight or of any other shape designed to best gain access to the fallopian tubes. Preferably the distal end portion 27 is curved and forms a portion, e.g. about 90°, of a circular arc in the unstressed condition to facilitate access to the ostia of fallopian tubes. Because the shape of the distal end portion 27 forms no part of this invention, it is shown for convenience as linear in FIGS. 2, 3, 5 and 7.

The outer catheter 13 may be of conventional construction, and the catheter body 19 may be constructed of a flexible, biocompatible polymeric material. The outer catheter fitting 21 has an injection leg 29 which is coupled to an inflation media source 31 for providing inflation media underpressure to the outer catheter lumen 23 to control the inversion and eversion of the everting element 17 in a known manner. The inflation media source 31 can be any known, or suitable, means for delivering inflation media under a suitable pressure to the everting element 17, such as a syringe or pump.

The inflation media may be, for example, water, saline solution, culture media or a contrast dye.

The inner catheter 15 is extendible through the outer catheter fitting 21 and is movable longitudinally in the outer catheter lumen 23. The inner catheter 15 also includes an elongated, flexible catheter body 33 of a suitable polymeric material and an inner catheter fitting 35. The inner catheter fitting 35 has a leg 37 which is coupled to a pressurized irrigation source 39 which provides flush solution under pressure and on demand through the inner catheter fitting 35 to an inner catheter lumen 41 (FIG. 2). The inner catheter lumen 41 extends axially for the full length of the inner catheter body 33 and opens at a distal opening 43 (FIG. 2) at a distal end 45 of the inner catheter body 33. Although the pressurized irrigation source 39 can take different forms as mentioned above, in this embodiment it is a peristaltic or syringe pump. Similarly, although there are a variety of flush solutions that can be used, in this embodiment the flush solution is a saline type solution or culture media.

The everting element 17 is a thin, flexible membrane which is constructed of a suitable polymeric material. The everting element 17 is bonded as by a suitable adhesive to the catheter body 19 of the outer catheter 13 closely adjacent the distal opening 25 and to a distal tip region of the catheter body 33 of the inner catheter 15 in accordance with known techniques. This forms a chamber 47 with the catheter body 19. Consequently, inflation media from the source 39 acting in the chamber 47 can bring about inversion and eversion of the everting element 17. The everting element 17 has a distal end 49. The everting element 17 forms a coaxial extension 51 of the inner catheter lumen 41. In this embodiment, the outer catheter 13 and the inner catheter 15 may be of conventional construction, if desired.

In carrying out the method of this invention in accordance with FIGS. 1-4, a substance 51, which may be in the form of a liquid globule or a pellet, is provided within the everting element 17 of the everting catheter 11 by appropriately loading the substance into the everting element. This can be accomplished, for example, by pressurizing the chamber 47 with inflation media from the source 31 to evert the everting element to an everted position as shown by way of example in FIG. 2. By placing the substance 51 at the distal end 49 and then reducing the pressure of the inflation media and inverting the everting element 17 as shown for example in FIG. 3, the everting element is caused to grip and capture the substance 51 and to retract it within the catheter body 19.

Figure 3:
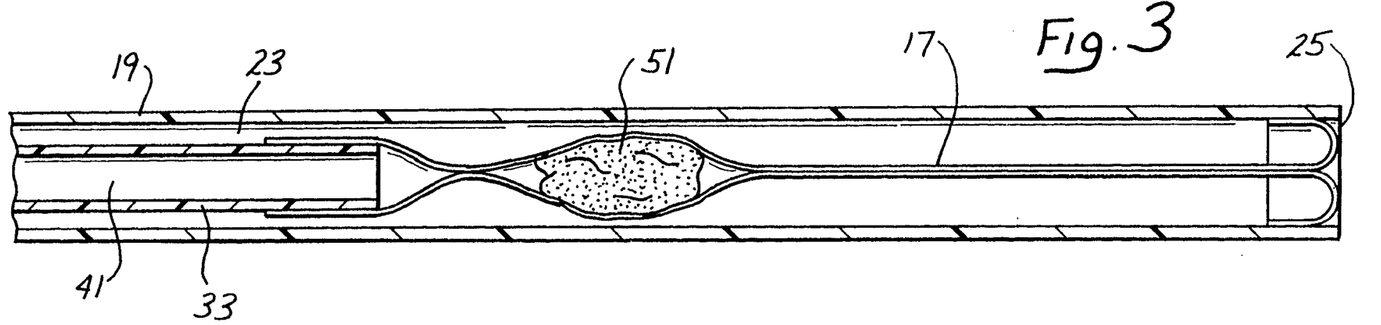
FIG. 3 is a view similar to FIG. 2 with the substance loaded into the everting catheter and with the everting element inverted.
Figure 4:
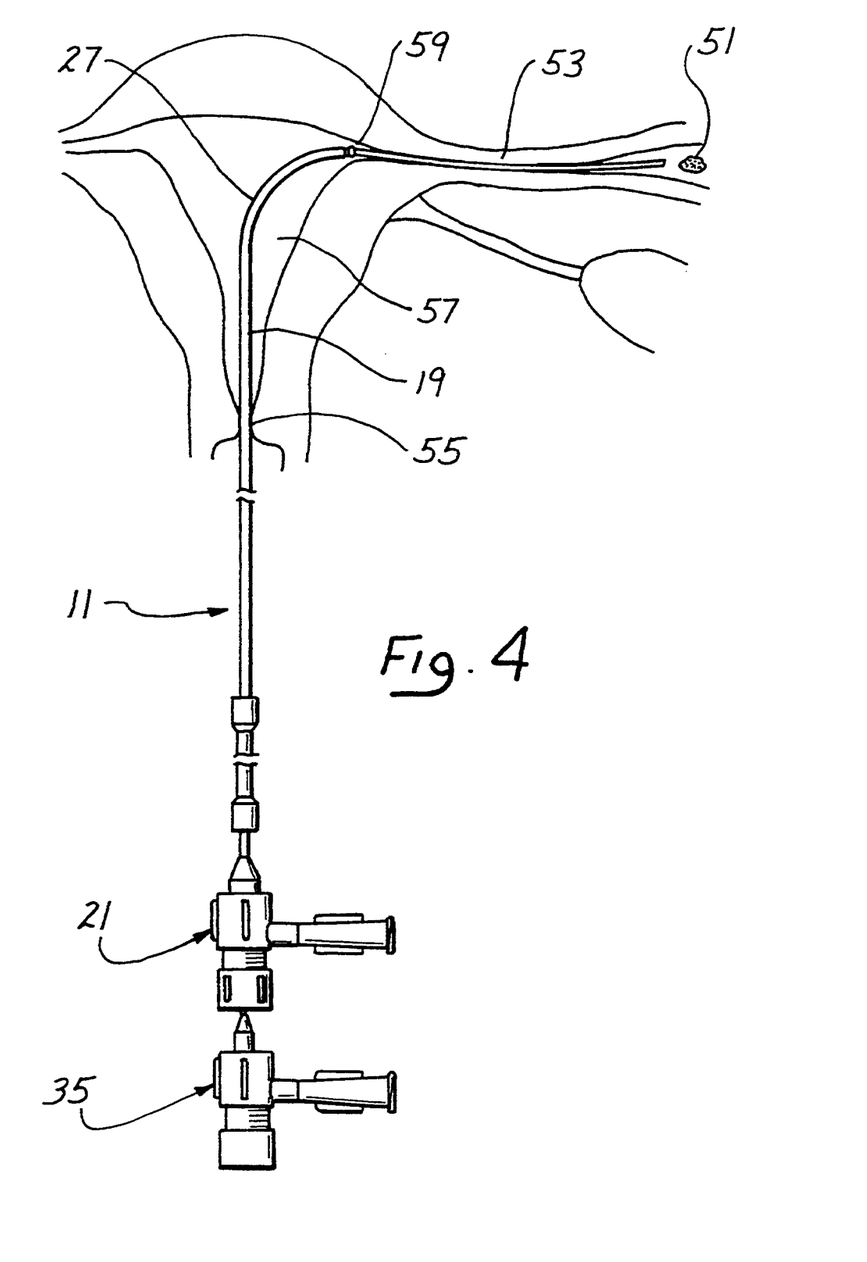
FIG. 4 is a plan view of the everting catheter with the catheter accessing a fallopian tube.

With the everting element 17 inverted and the substance 51 isolated within the everting element 17 and the catheter body 19 as shown in FIG. 3, the catheter body 19 can be used to obtain transcervical access to a fallopian tube 53 as shown in FIG. 4 by inserting the catheter body through the cervix 55 and the uterus 57 to an ostium 59 of the fallopian tube 53. The curved distal end portion 27 of the catheter body assists in locating the ostium 59. If desired, the everting catheter 11 may be of the type shown and described in common assignee's copending application Ser. No. 780,871 filed Oct. 18, 1991 and access to the ostium 59 can be obtained in the manner described in that copending application.

With the distal opening 25 positioned at the ostium 59, inflation media from the source 31 is again supplied through the outer catheter lumen 23 to the chamber 47 to evert the everting element 17. This moves the substance 51 through the outer catheter lumen 23 of the catheter body 19 and out through the distal opening 25 and eventually out of the distal end 49 of the everting element 17 to thereby deposit the substance 51 in the fallopian tube 53.

During the entire procedure and up until the moment of depositing of the substance 51 in the fallopian tube 53, the substance is retained in and protected by the catheter body 19 and/or the everting element 17. The region of the fallopian tube 53 in which the substance 51 is deposited can be controlled by controlling the position of the substance 51 within the everting element 17. Specifically, the extent to which the everting element is everted when the substance 51 is placed at the distal end 49 is the same length that the everting element must be everted in the fallopian tube 53 in order to deposit the substance 51. In this fashion, the region of the fallopian tube 53 in which the substance 51 is deposited can be selected.

As indicated above, the substance 51 can be either biological material such gametes or zygotes or a cytotoxic agent for treating and ectopic pregnancy. In the latter case it is desirable to deposit the cytotoxic agent at the location of the ectopic pregnancy.

Figures 5, 6:
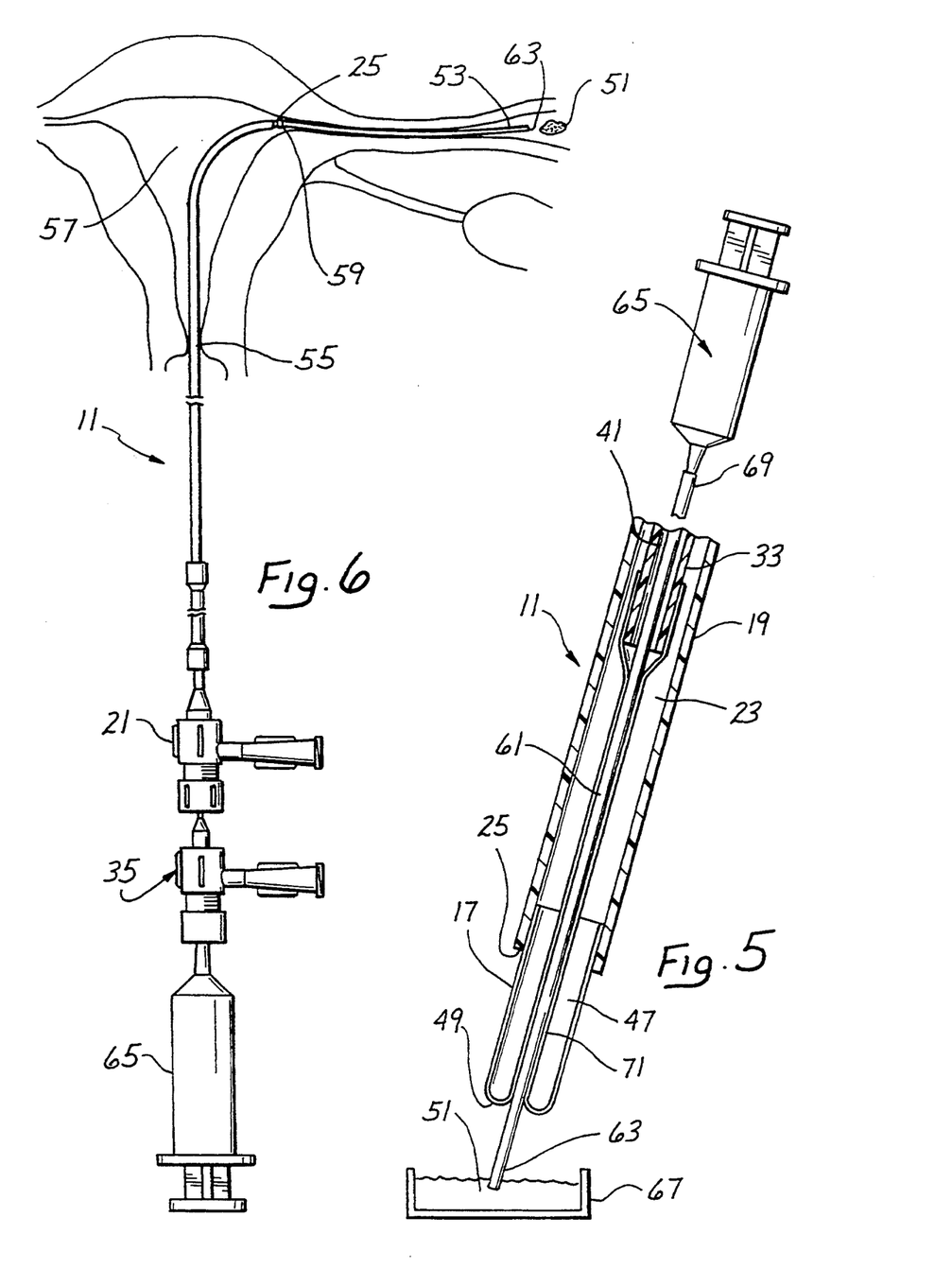
FIG. 5 is a fragmentary, axial sectional view through a distal region of an everting catheter and a delivery catheter with the latter being shown in elevation.
FIG. 6 is a view similar to FIG. 4 with the everting catheter and delivery catheter accessing a fallopian tube to deposit a substance in the fallopian tube.

FIGS. 2 and 3 illustrate one way to provide the substance 51 within the everting catheter 11 before obtaining transcervical access to a fallopian tube and with the everting catheter outside the body of the patient. A second technique for accomplishing this is shown in FIG. 5 in which an elongated flexible delivery catheter 61 is inserted through the entire length of the everting catheter 11 and the substance 51 is loaded into a distal end 63 of the delivery catheter. More specifically, the delivery catheter 61 is inserted through the inner catheter lumen 41 and everting element 17 so that the distal end 63 of the delivery catheter extends beyond the distal end 49 of the everting element. As shown by way of example in FIG. 5, the distal end 63 of the delivery catheter 61 is placed into or adjacent some of the substance 51 and a suitable delivery device, such as a syringe 65 is operated to suck a desired quantity of the substance 51 from a receptacle 67 into the distal end of the delivery catheter 61 and/or into the syringe.

The delivery catheter 61 is preferably a single lumen catheter and may be, for example, a cylindrical tube having a cylindrical axial passage extending completely through it. The delivery catheter 61, or at least the portion thereof which comes into contact with the substance 51, should be inert with respect to the substance. In the case where the substance 51 is biological material, the delivery catheter 61 is preferably constructed of polytetrafluoroethylene. The syringe 65 which is coupled to a proximal end 69 of the delivery catheter 61 is proximal to the inner catheter fitting 35 as shown in FIG. 6.

The everting catheter 11 and delivery catheter 61 of FIG. 5 can be used in at least two different ways. The everting catheter 11 with the delivery catheter 61 within it can then be inserted through the cervix 55 and the uterus 57 (FIG. 6) to position the distal opening 25 substantially at the ostium 59 of the fallopian tube 53 as described above in connection with FIG. 4. The everting element 17 is then everted into the fallopian tube 53 and this carries the delivery catheter 61 with it. When the desired location has been reached, the syringe 65 is operated to apply sufficient fluid pressure to the substance 51 to eject it from the distal end 63 of the delivery catheter 61 and deposit it in the fallopian tube 53.

Thus, the delivery of the substance 51 is carried out through the delivery catheter 61.

Alternatively, the substance 51 can be loaded into the distal end 63 of the delivery catheter 61 before inserting the delivery catheter into the everting catheter 17. In this event, the everting catheter 11 with the everting element 17 inverted may be inserted through the cervix 55 and the uterus 57 to position the distal opening 25 at the ostium 59. Then the delivery catheter 61 can be inserted through the inner catheter lumen 41 and to a desired position within the everting element 17. Insertion of the delivery catheter 61 into the everting element 17 is possible when the everting element is deflated. Thereafter, the everting element 17 can be everted into the fallopian tube 53 to position the delivery catheter 61 at the desired region of the fallopian tube 53 and to enable the delivery catheter to deposit the substance 51 in the fallopian tube 53 as described above. Alternatively, the delivery catheter 61 can be inserted through the everting catheter 11 after the everting element 17 is everted into the fallopian tube 53. The delivery catheter 61 and the inner catheter 15 may have indicia (not shown) which can be used as set forth in Woker et al U.S. Pat. No. 5,163,927 to identify the location of the distal end 63 relative to the distal end 49.

It can be seen in FIG. 5 that the everting element 17 grips a region 71 of the delivery catheter 61. Because the delivery catheter 61 is gripped by the everting element 17 as the everting element everts, the everting element also pulls the delivery catheter 61 along in the fallopian tube 53. This gripping of the region 71 of the delivery catheter 61 by the everting element 17 prevents, or substantially prevents, moving of the delivery catheter 61 relative to the everting element, and in particular, it prevents relative longitudinal movement of the delivery catheter and the everting element.

Figure 7:
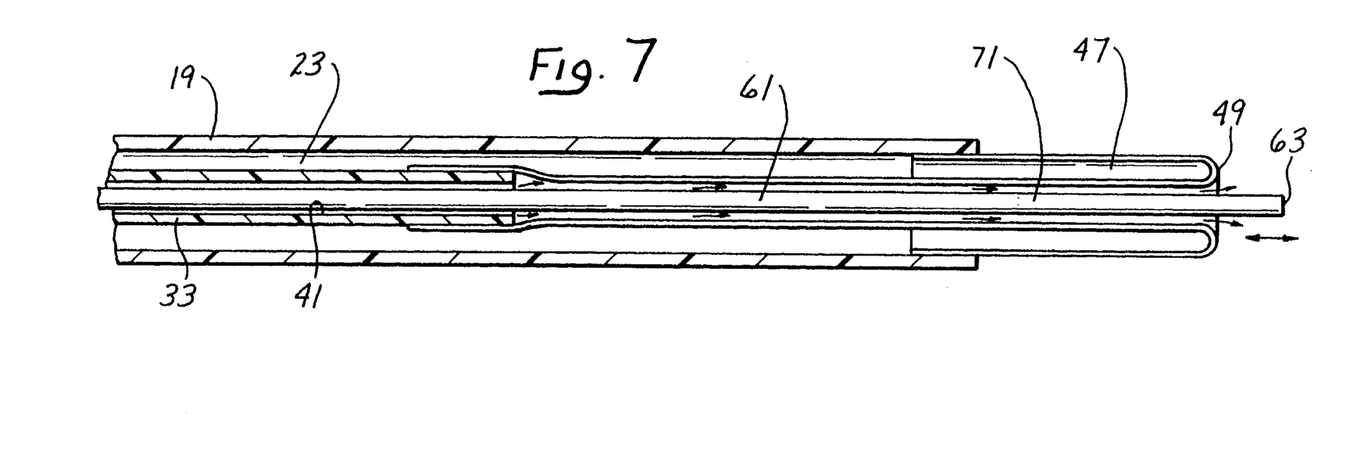
FIG. 7 is an axial sectional view similar to FIG. 5 illustrating a preferred technique for moving of the delivery catheter relative to the everting element.

In order to position the delivery catheter 61 as desired in the fallopian tube 53, it is necessary to move the delivery catheter independently of the everting element 17. Although this can be accomplished in various was such as by deflating of the everting element 17, preferably this is accomplished utilizing flush solution from the irrigation source 39 (FIG. 1). This flush solution is introduced through the inner catheter fitting 35 and the inner catheter lumen 41 and between the everting element 17 and the delivery catheter 61 where the everting element grips the delivery catheter, i.e. at the region 71. The flush solution lubricates the interface between the everting element 17 and the delivery catheter 61 at the region 71 and may form a layer of flush solution for the full length of the region 71 and completely circumferentially around the region 71. As such, this flush solution separates the everting element 17 and the delivery catheter 61 at the region 71. The flush solution preferably flows completely through the region 71 and exits out the distal end 49 of the everting element 17 as shown in FIG. 7. Because the flush solution between the everting element 17 and the delivery catheter 61 in the region 71 separates the everting element and the delivery catheter as shown in FIG. 7, the delivery catheter can be moved relative to the everting element. Such movement of the delivery catheter 61 may be rotational and/or longitudinal but typically is longitudinal so as to more desirably position the distal end 63 of the delivery catheter at a region of the fallopian tube 53 where it is desired to deposit the substance.

In order to obtain the flow of flush solution between the everting element 17 and the delivery catheter 61 at the region 71, the pressure of the flush solution from the irrigation source 39 is preferably greater than the pressure of the inflation media in the chamber 47. For example, if the inflation media is at 4 atmospheres, the pressure of the flush solution provided by the irrigation source 39 may be slightly above 4 atmospheres.

Figure 8:
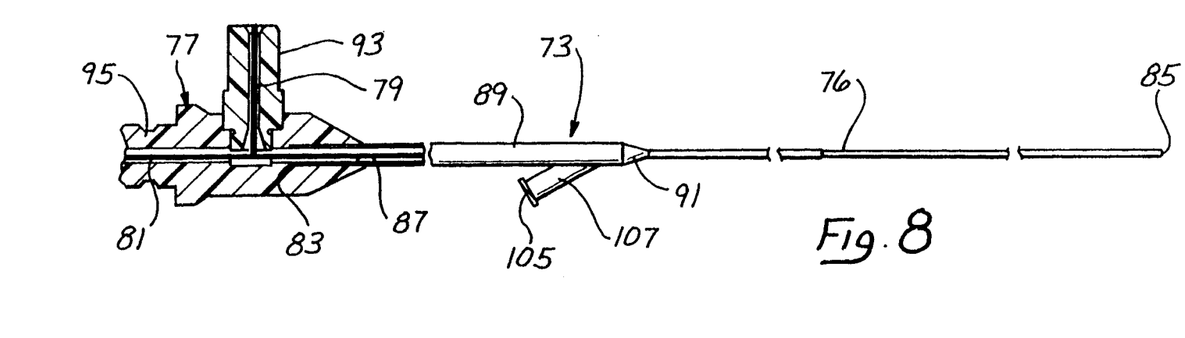
FIG. 8 is an elevational view partially in section of a delivery catheter which includes an endoscope.
Figure 9:
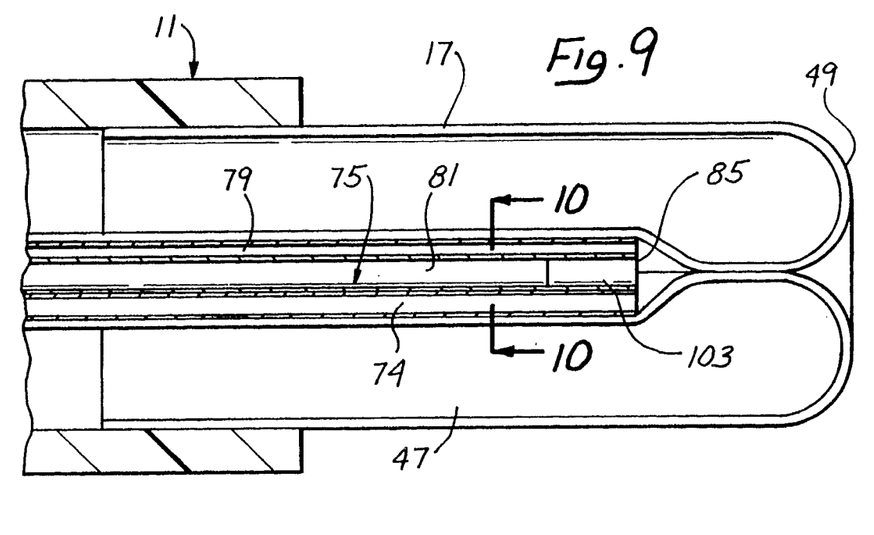
FIG. 9 is an enlarged, fragmentary, axial sectional view of a distal region of the delivery catheter and a distal region of an everting catheter with the everting element partially everted.
Figure 10:
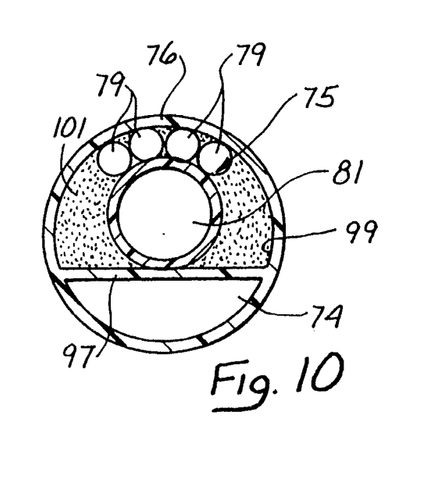
FIG. 10 is an enlarged sectional view taken generally along line 10—10 of FIG. 9.

The method of this invention may also employ an endoscope and/or a delivery catheter which includes an endoscope. FIGS. 8–10 illustrate a delivery catheter 73 which includes both a working lumen 74 (FIGS. 9 and 10) and an elongated endoscope 75 (FIGS. 9 and 10).

The everting catheter 11 can be used with the delivery catheter 73 in an everting catheter system to provide certain features of this invention. The delivery catheter 73 includes an elongated, flexible body 76 and a hub 77. The delivery catheter 73 also includes one or more illumination fibers 79 and image or visualization fibers 81.

The body 76 has a proximal end 83 and a distal end 85. The proximal end 83 is received within an axial passage 87 of the hub 77. A strain relief tube 89 receives a region of the body 76 adjacent the proximal end 83 and the strain relief tube is also received within the passage 87. An adhesive 91, such as urethane adhesive, joins the body 76 to the tube 89. The body 76 and tube 89 are affixed to the hub 77 in any suitable manner, such as by a urethane adhesive.

The illumination fibers 79 extend from the distal end 85 through the full length of the body 76, into the passage 87 and through a leg 93 or illumination connector of the hub 77 which is adapted to be coupled to a light source (not shown). Similarly, the image fibers 81 extend from the distal end 85 through the full length of the body 76 into the passage 87 and into a leg 95 of the hub 77. A suitable adhesive, such as an epoxy adhesive may be used to bond the ends of the fibers 79 and 81 to the legs 93 and 95, respectively. Although the leg 95 could be adapted for coupling to an eyepiece (not shown) to permit direct visualization, in this embodiment it is adapted for coupling to a camera (not shown) to enable the image to be viewed on a monitor. The delivery catheter 73 and the inner catheter 15 may have indicia (not shown) which can be used as set forth in Woker et al U.S. Pat. No, 5,163,927 to identify the location of the distal end 85 relative to the distal end 49.

As shown in FIG. 10, the body 76 is cylindrical and includes a wall 97 which separates the interior of the body 76 into the working lumen 74 and an endoscope lumen 99 in which the fibers 79 and 81 of the endoscope are located and held in position by a suitable potting compound 101. A distal lens 103 (FIG. 9) is provided at the distal end of the image fibers 81 in the usual manner for endoscopes. The working lumen 74 extends from the distal end 85 of the delivery catheter 73 to a port 105 in a leg 107 of the strain relief tube 89. The working lumen 74 is blocked off in the body 76 proximally of the leg 107.

The delivery catheter 73 can be used with the everting catheter 11 in the ways described above for the delivery catheter 61, and in addition, the delivery catheter 73 can be used for viewing of the fallopian tube 53 (FIGS. 4 and 6) distally of the everting catheter and distally of the everting element 17. The endoscope 75 of the delivery catheter 73 can be used to view the fallopian tube 53 to locate a desired region of the fallopian tube, such as the location of an ectopic pregnancy or a location at which biological material is to be deposited. The substance 51 can be delivered directly through the working lumen 74 to such desired region of the fallopian tubes. This delivery can be accomplished by fluid pressure utilizing a syringe, such as the syringe 65, (FIG. 5) and by coupling that syringe to the leg 107 (FIG. 8) at the port 105. Alternatively a separate tube (not shown), such as the delivery catheter 61, can be inserted through the port 105 and the working lumen 74, and the substance 51 can be delivered through such tube.

The everting catheter 11 can deliver the delivery catheter 73 into the fallopian tube utilizing the techniques described above in connection with FIG. 6 and the delivery catheter 73 can be positioned axially with respect to the everting element 17 as described above in connection with FIG. 7. The distal end 85 of the delivery catheter 73 should extend sufficiently through the everting catheter 11 so it can be used for viewing of the fallopian tube 53 distally of the everting element 17. For this purpose, the distal end 85 is preferably at or closely adjacent the distal end 49 of the everting element. The distal end 85 may be somewhat proximal of the distal end 49 for those cases in which the everting element 17 is sufficiently transparent to permit viewing through a region of the everting element.

Another feature of this invention is to utilize an endoscope without the working lumen 74 and to deliver the endoscope into the fallopian tube 53 (FIG. 6) with the everting catheter 11 to locate a desired region of the fallopian tube. The endoscope is then withdrawn from the patient leaving the everting catheter in place within the fallopian tube. Thereafter, the substance 51 is delivered, either utilizing a delivery catheter, such as the delivery catheter 61, or without using a delivery catheter in which event the substance is delivered directly through the inner lumen 41 and the everting element 17 of the everting catheter to the desired location which was located by the endoscope. A pressure source such as a syringe may be used to propel the substance 51 directly through the everting catheter 11 or through the delivery catheter 61.

Figure 11:
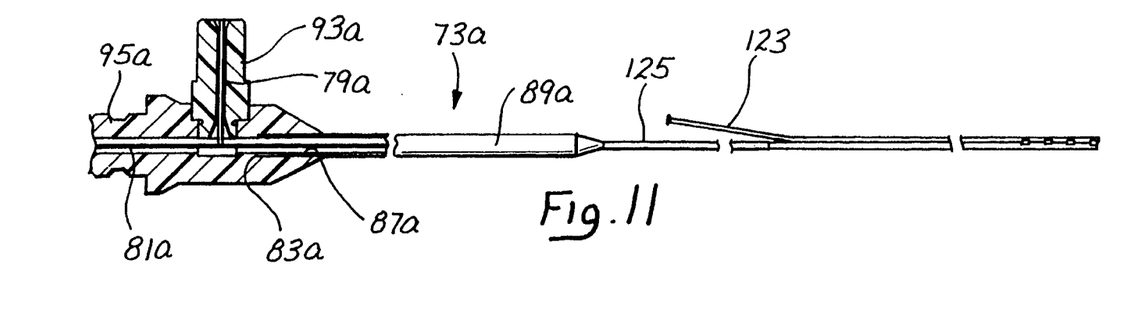
FIG. 11 is an elevational view partially in section of a second form of delivery catheter which comprises both a tube and an endoscope.
Figure 12:
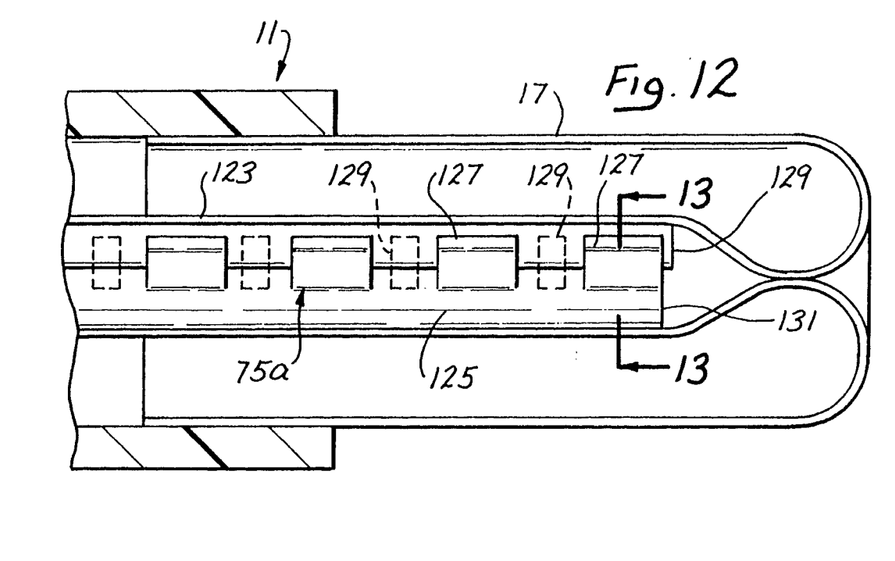
FIG. 12 is a sectional view similar to FIG. 9 showing a distal region of an everting catheter and a distal region of the delivery catheter of FIG. 11.
Figure 13:
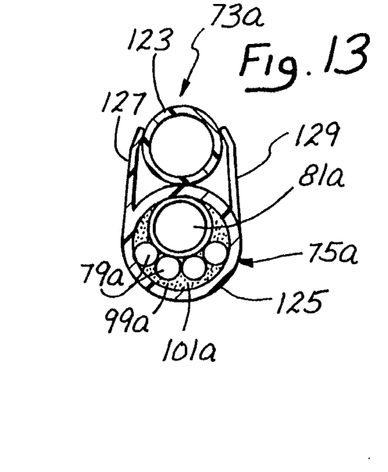
FIG. 13 in an enlarged sectional view taken generally along line 13—13 of FIG. 12.

FIGS. 11-13 show a delivery catheter 73a which is identical to the delivery catheter 73 in all respects not shown or described herein. Portions of the delivery catheter 73a corresponding to portions of the delivery catheter 73 are designated by corresponding reference numerals followed by the letter "a". The delivery catheter 73a includes an elongated flexible endoscope 75a and an elongated flexible tube 123 removably coupled to the endoscope. The endoscope 75a includes an endoscope body 125, which may be cylindrical and which contains only the endoscope lumen 99a. The illumination fibers 79a, the imaging fibers 81a, the potting compound 101a and a distal lens (not shown) which may be identical to the distal lens 103 (FIG. 9) are provided within and fill the endoscope lumen 99a.

The tube 123 may be identical to the delivery catheter 63. Although the tube 123 can be removably coupled to the endoscope body 125 in various different ways, in this embodiment it is accomplished by spaced resilient arms 127 and 129 which extend in the same general direction from the endoscope body in spaced relationship. The tube 123 can be snapped between the oppositely facing arms 127 and 129 as shown in FIGS. 12 and 13 to removably attach the tube to the endoscope body 125. In this embodiment, the arms 127 and 129 are integral with the endoscope body 125, and they releasably grip the tube 123. The endoscope body 125 may be constructed of a suitable polymeric material such as Teflon coated polyimide. When the tube 123 is to be used to deposit biological material, inert material such as polytetrafluoroethylene can be used for the tube 123.

The tube 123 has a distal end 129 (FIG. 12) which is preferably closely adjacent and may lie in substantially the same plane as a distal end 131 of the endoscope body 125. The tube 123 extends proximally along the endoscope body 125 for a substantial length of the endoscope body and the arms 127 and 129 extend for a similar substantial distance.

The delivery catheter 73a may be used in the same manner as described above for the delivery catheter 73. Thus, access to the fallopian tube 53 is accomplished with the everting catheter 11 and viewing of the fallopian tube 53 is accomplished with the endoscope 75a. The substance 51 is delivered through the tube 123 to the desired region of the fallopian tube. The proximal end of the tube 123 can be coupled to a syringe or other suitable device for expelling the substance in the tube into the fallopian tube. Upon completion of the deposition, the everting catheter 11 which was used to deliver the delivery catheter 73a to the desired location within the fallopian tube and the delivery catheter are removed from the patient. The tube 123 is then removed from the endoscope 75a and disposed of and the endoscope portion of the delivery catheter 73a together with the arms 127 and 129 are sterilized for reuse.

Although exemplary embodiments of the invention have been shown and described, many changes, modifications and substitutions may be made by one having ordinary skill in the art without necessarily departing from the spirit and scope of this invention.

We claim:

1. A method of delivering a substance to a fallopian tube of a patient comprising:
    obtaining transcervical access to a fallopian tube with an everting catheter;
    said step of obtaining including everting an everting element of the everting catheter in the fallopian tube; and
    delivering a substance selected from the group consisting of biological material and cytotoxic agents through the everting catheter into the fallopian tube to deposit the substance in the fallopian tube.

2. A method as defined in claim 1 wherein the substance is gametes.

3. A method as defined in claim 1 wherein the substance is embryos.

4. A method as defined in claim 1 wherein the substance is a cytotoxic agent.

5. A method as defined in claim 1 including retracting the everting catheter from the fallopian tube leaving the substance in the fallopian tube.

6. A method as defined in claim 1 including providing the substance within the everting catheter prior to the step of obtaining and with the everting element inverted and the step of delivering includes everting the everting element in the fallopian tube sufficiently to deposit the substance in the fallopian tube.

7. A method as defined in claim 1 including inserting an elongated flexible delivery catheter through a substantial length of the everting catheter and carrying out said step of delivering through the delivery catheter.

8. A method as defined in claim 7 including loading the substance into a distal end of the delivery catheter with the delivery catheter extending into the everting catheter and beyond a distal end of the everting catheter.

9. A method as defined in claim 7 including loading the substance into a distal end of the delivery catheter, said step of obtaining includes inserting the everting catheter through the cervix and uterus of a patient to place a distal end of the everting catheter near an ostium of a fallopian tube, and inserting the delivery catheter with the substance loaded therein through said substantial length of the everting catheter following the insertion of the everting catheter through the cervix and uterus.

10. A method as defined in claim 9 wherein the insertion of the delivery catheter is carried out after the step of everting.

11. A method as defined in claim 7 wherein the delivery catheter includes an elongated flexible endoscope extending sufficiently through the everting catheter so it can be used for viewing of the fallopian tube distally of the everting catheter, the method includes viewing the fallopian tube with the endoscope to locate a desired region of the fallopian tube and the step of delivering includes delivering the substance through the delivery catheter to said desired region.

12. A method as defined in claim 11 wherein the endoscope has a working lumen and the step of delivering includes delivering the substance through the working lumen to said desired region.

13. A method as defined in claim 11 wherein the delivery catheter includes an elongated, flexible tube removably coupled to the endoscope and the step of delivering includes delivering the substance through the tube to said desired region.

14. A method as defined in claim 13 including disposing of the tube and sterilizing the endoscope after the step of delivering.

15. A method as defined in claim 7 wherein there is a delivery device coupled to the delivery catheter and including loading the substance into at least one of the delivery device and the delivery catheter prior to said step of delivering.

16. A method as defined in claim 1 including extending an elongated flexible endoscope sufficiently through an everting catheter so it can be used to view the fallopian tube distally of the everting catheter, viewing the fallopian tube with the endoscope to locate a desired region of the fallopian tube and said step of delivering includes depositing the substance at said desired region.

17. A method as defined in claim 16 including withdrawing the endoscope prior to said step of delivering.

18. A method as defined in claim 17 wherein the step of delivering is carried out directly through the everting catheter without a delivery catheter.

19. A method as defined in claim 17 including inserting an elongated delivery catheter through a substantial length of the everting catheter subsequent to the step of withdrawing and carrying out the step of delivering through the delivery catheter.

20. A method of delivering a substance to a fallopian tube of a patient comprising:

inserting an everting catheter which includes an outer catheter having an outer catheter lumen, an inner catheter movable in the outer catheter lumen and having an inner catheter lumen and an everting element coupled to the outer and inner catheters through the cervix and uterus of a patient to a location adjacent an ostium of the fallopian tube;

everting the everting element into the fallopian tube;

providing an endoscope within the inner catheter lumen and within the everting element;

viewing the fallopian tube with the endoscope to locate a desired region of the fallopian;

withdrawing the endoscope; and delivering a substance selected from the group consisting of biological material and cytotoxic agents through the inner catheter lumen to the fallopian tube to deposit the substance at said desired region.

21. A method as defined in claim 20 including inserting an elongated flexible delivery catheter through a substantial length of the inner catheter lumen subsequent to said step of withdrawing and carrying out said step of delivering through the delivery catheter.

22. A method as defined in claim 20 wherein the desired region is the location of an ectopic pregnancy and said substance is a cytotoxic agent.

23. A method as defined in claim 20 wherein the desired region is a location where it is desired to implant biological material and said substance is biological material.

24. A method as defined in claim 20 wherein the everting element circumscribes a region of the endoscope and is inflatable to grip the endoscope and said step of providing includes introducing a flush solution between the everting element and the endoscope where the everting element grips the endoscope and moving the endoscope relative to the everting element while the flush solution between the everting element and the endoscope.

* * * * *